United States Patent
Ben Chaabane et al.

(10) Patent No.: US 10,214,734 B2
(45) Date of Patent: Feb. 26, 2019

(54) METHOD FOR PRODUCING AN ENZYMATIC COCKTAIL FROM FUNGAL MUST

(71) Applicant: IFP Energies nouvelles, Rueil-Malmaison (FR)

(72) Inventors: Fadhel Ben Chaabane, Paris (FR); Etienne Jourdier, Bougival (FR); Celine Cohen, Paris (FR); Bernard Chaussepied, Hanches (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/500,299

(22) PCT Filed: Jul. 27, 2015

(86) PCT No.: PCT/EP2015/067139
§ 371 (c)(1),
(2) Date: Jan. 30, 2017

(87) PCT Pub. No.: WO2016/016182
PCT Pub. Date: Feb. 4, 2016

(65) Prior Publication Data
US 2017/0211051 A1     Jul. 27, 2017

(30) Foreign Application Priority Data
Jul. 30, 2014  (FR) ...................... 14 57358

(51) Int. Cl.
| | |
|---|---|
| *C12N 1/06* | (2006.01) |
| *C12N 1/14* | (2006.01) |
| *C12N 9/24* | (2006.01) |
| *C12N 9/42* | (2006.01) |

(52) U.S. Cl.
CPC ............. *C12N 9/2445* (2013.01); *C12N 1/06* (2013.01); *C12N 1/14* (2013.01); *C12N 9/248* (2013.01); *C12N 9/2437* (2013.01); *C12Y 302/01021* (2013.01); *C12Y 302/01037* (2013.01); *Y02E 50/16* (2013.01)

(58) Field of Classification Search
CPC combination set(s) only.
See application file for complete search history.

(56) References Cited

PUBLICATIONS

International Search Report for PCT/EP2015/067139 dated Oct. 19, 2015.

Roussos, S. et al., "Hydrolyse de la cellulose par les moisissures II. Harzianum par Fermentation en Milieu Liquide," Annales de Microbiologie, Jan. 1, 1982, vol. 133, pp. 465-474.

Pitson et al., "Induction and carbon source control of extracellular beta-glucosidase production in Acremonium persicinum," Mycological Research, Feb. 1, 1999, vol. 103, No. 2, pp. 161-167.

Rao, M. et al., "Laminarinase from penicillium-funiculosum and its role in release of beta glucosidase," Biotechnology and Applied Biochemistry, Jan. 1, 1991, vol. 13, No. 2, pp. 277-285.

Copa-Patino, J. et al., "Purification and properties of a beta-glucosidase from penicillium oxalicum autolysates," Fems Microbiology Letters, Jan. 15, 1990, pp. 191-196.

Gaikwad et al., "Localization and release of beta-glucosidase in the thermophilic and cellulolytic fungus, *Sporotrichum thermophile*," Experimental Mycology, Dec. 1, 1994, vol. 18, No. 4, pp. 300-310.

Mukhopadhyay, S. N. et al., "Increased production of cellulase of *Trichoderma* sp. by pH cycling and temperature profiling," Biotechnology and Bioengineering, Jan. 1, 1980, vol. 22, No. 11, pp. 2237-2250.

Kubicek, C. P. et al., "Beta glucosidase excretion by trichoderma-pseudokoningii correlation with cell wall bound beta-1.3 glucanase EC-3.2.1.6 activities," Archives of Microbiology, 1982, vol. 132, No. 4, pp. 349-354.

Egyhazi, A. et al., "Examination of cellulose enzyme production by Trichoderma Reesei rut C30 using supercritical carbon dioxide cell disruption," Chemical and Biochemical Engineering Quarterly, Jan. 1, 2004, vol. 18, No. 3, pp. 257-261.

Martinez, M. J. et al., "beta-Glucosidase from the cellulolytic system of Alternaria alternata autolyzed cultures," Fems Microbiology Letters, Oct. 15, 1988, vol. 55, No. 3, pp. 263-267.

Umile, C. et al., "A constitutive, plasma-membrane bound beta-glucosidase in Trichoderma reesei," Fems Microbiology Letters, May 1, 1986, vol. 34, No. 3, pp. 291-295.

*Primary Examiner* — Kagnew H Gebreyesus
(74) *Attorney, Agent, or Firm* — Millen, White, Zelano and Branigan, P.C.

(57) ABSTRACT

The invention relates to a process for the production of an enzymatic cocktail from a cellulolytic microorganism producing cellulases and/or hemi-cellulases, comprising:

a step for the production of enzymes with a medium being obtained containing enzymes and a microorganism must, said must is separated, or not separated, from the liquid containing said enzymes, a step of cooling said must to a temperature below the temperature of the enzyme production step and for a time such that the beta-glucosidase concentration of the liquid originating from the cooling step is greater than that of the liquid originating from the enzyme production step, and/or the solid volume/total volume ratio is less than said ratio for the enzyme production step, and an enzymatic cocktail is obtained at the end of the cooling step.

18 Claims, 6 Drawing Sheets derma reesei, owing to its high secretion capacity. In the conventional processes for the production of cellulases, these are recovered in the culture supernatant via several separation steps.

METHOD FOR PRODUCING AN ENZYMATIC COCKTAIL FROM FUNGAL MUST

The present invention relates to improving the production of cellulolytic and/or hemicellulolytic enzymes, in particular within the context of the production of ethanol from cellulosic or lignocellulosic materials.

These latter are produced from lignocellulosic biomass and, as far as the use of agricultural land for the production of bio-fuels is concerned, pose fewer problems of competition with food production, than the processes for so-called first-generation products based on sugar cane, maize, wheat, beet etc.

The various technical-economic studies demonstrate that the reduction in the cost of the cellulases is one of the key factors of the processes for the biological production of ethanol starting from lignocellulosic raw materials.

At present, industrial cellulases are mainly produced by a filamentous fungus, *Trichoderma reesei*, owing to its high secretion capacity. In the conventional processes for the production of cellulases, these are recovered in the culture supernatant via several separation steps.

The fungal must (solid part recovered after filtration) is not reused. It is regarded as waste.

Furthermore, the enzymatic cocktail produced by the hyper-producing strains of *Trichoderma reesei* is lacking in terms of β-glucosidase activity.

Patents have proposed processes for improving the producing strain in several ways: by overexpressing the gene (such as patent application EP2082054 relating to the overexpression of a β-glucosidase), or by cloning more effective β-glucosidases originating from other microorganisms (such as patent application WO2013115305 which describes the cloning of the β-glucosidase gene of *Aspergillus* in *Trichoderma reesei*) or also by creating more effective new genes from different genes of β-glucosidase (such as patent application WO2010029259 which describes the production of variants of β-glucosidase with improved activity by L-Shuffling).

It is also known from patent application WO11079048 that, in an SSF process (simultaneous hydrolysis and fermentation), the increase in β-xylosidase activity has a beneficial effect on enzymatic hydrolysis since it makes it possible to reduce the dose of enzymes used. It also makes it possible to hydrolyze the alkyl xylosides. The invention proposes a process for the production of an enzymatic cocktail and an installation suitable for implementing the process according to the invention, a cocktail which makes it possible to significantly, or even dramatically, increase β-glucosidase and β-xylosidase activities.

Surprisingly, it has been found that the implementation of the process according to the invention leads to a significant improvement in the specific activity of β-glucosidase, FPase and β-xylosidase. β-glucosidase activity can be between 3 and 10 times greater than that measured at the end of enzyme production under normal conditions; that of β-xylosidase, 3 times greater.

The fungal must which is separated from the enzymes during a conventional enzyme production step is therefore reused; this must represents 10-20% by mass with respect to the total mass of the culture.

More precisely, the invention relates to a process for the production of an enzymatic cocktail from a cellulolytic microorganism producing cellulases and/or hemi-cellulases, comprising:

- a step for the production of enzymes with a medium being obtained containing enzymes and a microorganism must; said must is separated, or not separated, from the liquid containing said enzymes,
- a step of cooling said must to a temperature comprised between 4 and 20° C. which is a temperature below the temperature of the enzyme production step, for a time such that:
  - the β-glucosidase or β-xylosidase concentration of the liquid originating from the cooling step is greater than that of the liquid originating from the enzyme production step, and/or
  - the solid volume/total volume ratio is less than said ratio for the enzyme production step,
- and an enzymatic cocktail is obtained at the end of the cooling step.

Advantageously, the temperature of the cooling step is comprised between 4 and 20° C., and preferably between 4° C. and 18° C.

Preferably, the cooling step is carried out at a pH comprised between 3.5 and 5.5, and preferably greater than 4.

In a preferred manner, the cooling step is carried out in an atmosphere depleted of oxygen, preferably in an anaerobic atmosphere.

Generally, a neutral gas, for example nitrogen or carbon dioxide, is injected.

Preferably, the microorganism belongs to the genus *Trichoderma*, in particular *Trichoderma reesei*, and is preferably the strain CL847.

After the cooling step, the enzymatic cocktail originating from the must is separated and a residual must is obtained.

Generally, the separation takes place by means of at least one centrifugation or filtration/pressing or microfiltration, optionally preceded by settling.

The enzymes in the separated liquid can be concentrated, for example by ultrafiltration.

The microorganism used is selected from the cellulolytic fungi or other modified microorganisms. In a preferred manner, the cellulolytic microorganism belongs to the genera *Trichoderma*, *Aspergillus*, *Penicillium* and *Schizophyllum* which produce in particular the cellulases and hemicellulases suitable for the total hydrolysis of cellulose and hemicelluloses.

The industrial strains used belong, in a preferred manner, to the species *Trichoderma reesei*; the fungus has been generally modified in order to improve the production of cellulolytic and/or hemicellulolytic enzymes by mutation-selection processes (random mutagenesis), such as for example the strain IFP CL847 (French patent FR-B-2 555 803). These strains are well known to a person skilled in the art.

The process according to the invention comprises an enzyme production step with a medium being obtained containing enzymes and a microorganism must, and with an optional separation of said must from the liquid containing the enzymes.

The strains are cultured in a stirred and aerated fermenter under conditions compatible with their growth and the production of the enzymes; these conditions are known to a person skilled in the art. A source of carbon for growth and an inductive source for the production of enzymes are introduced. The carbon source can be an industrial soluble sugar, for example glucose, lactose or xylose, or an extract from the hemicellulosic fraction in the form of monomers originating from the pretreated biomass. The inductive carbon source can be selected from lactose, cellobiose, sophorose, and cellulose. The hydrolysis residue or the pretreated lignocellulosic material can also be used as a source of carbon for the growth of the microorganism and the induction of the expression system. The latter carbon source can also be used by the genetically improved strains and in particular the recombinant strains.

At the end of the enzyme production step, the must is separated from the liquid or is not separated from the liquid or also only a part of the must can be separated. The must corresponds to the fungus, to the solid part. The liquid contains the enzymes. The separated must can be diluted (in whole or in part). The separated must is preferably diluted with water.

The separation can be adapted, in particular depending on the desired activities.

The separation can be carried out by any means known to a person skilled in the art. Preferably, at least one centrifugation or one filtration/pressing (filter-press) or microfiltration may be mentioned. The centrifugation is optionally preceded by settling. A step of concentrating the enzymes, for example by ultrafiltration, can be envisaged.

The process according to the invention continues with a step of cooling said must (separated or unseparated) to a temperature below the temperature of the enzyme production step and for a specific period.

The temperature of the cooling step is advantageously comprised between 4 and 20° C., and preferably between 4° C. and 18° C.

Preferably, the cooling step is carried out at a pH comprised between 3.5 and 5.5, and preferably greater than 4. This pH interval is defined between the pH 3 of the start of deactivation of the β-glucosidase and the pH 6 of possible sporulation of the fungus.

Preferably, the cooling step is carried out in an atmosphere depleted of oxygen, preferably in an anaerobic atmosphere. Generally, a neutral gas, for example nitrogen or carbon dioxide, is injected. An improved yield has been observed in an atmosphere depleted of oxygen, and the best yields are in an anaerobic atmosphere. In the presence of oxygen the fungus can again consume the enzymes.

Generally, cooling for at most 120 hours, preferably 12 hours to 90 hours, preferably 24 to 72 hours is sufficient, and generally approximately 48 hours.

During this cooling step, a reaction of autolysis of the fungus present in the must is established, autolysis generated by the enzymes. The latter are present either in the liquid of the unseparated must or they are those which are still held within the separated must and which have not been able to be separated.

It is noted experimentally that, under the conditions of the process according to the invention, the β-glucosidase and β-xylosidase activities increase very significantly and the biomass pellet reduces.

In order to optimize the yield of enzymatic cocktail, the cooling time can be determined beforehand in a laboratory test.

Advantageously, the cooling time is controlled during the implementation of the process, the progress of the reaction is monitored by taking samples.

The cooling time is such that
the β-glucosidase or β-xylosidase activity of the liquid originating from the cooling step is greater than that of the liquid originating from the enzyme production step, and/or
the solid volume/total volume (pellet of biomass) ratio is less than said ratio for the enzyme production step.

The substrate used in order to determine the β-glucosidase or aryl β-glucosidase activity is p-nitrophenyl-β-D-glucopyranoside (PNPG). It is cleaved by β-glucosidase which releases p-nitrophenol.

One unit of aryl β-glucosidase activity is defined as the quantity of enzyme required to produce 1 μmol of p-nitrophenol from PNPG per minute and is expressed in IU/mL.

The substrate used in order to determine the β-xylosidase activity is p-nitrophenyl-β-D-xylopyranoside according to the same principle.

These parameters are determined from measurements.

It has been observed that, during the process, the concentration of β-glucosidase increases, reaches a maximum then decreases. At the same time, it has been observed that the pellet of biomass decreases.

By way of example, it has been noted that generally the quantity of liquid released is equivalent to at least 10%, and most often 30-40% of the original weight of the separated must and that the concentration of proteins, measured in terms of β-glucosidase and β-xylosidase activities, was multiplied by 3.

Determining the cooling time based on this information is within the competence of a person skilled in the art.

After the cooling step, the enzymatic cocktail (liquid part) can be separated, or not, from the residual solid; preferably it is separated.

The separation means are those described previously.

It has been noted that this separation is more difficult, more delicate when the must has not been separated right at the end of the culture.

Also, in a very preferred manner, a separation of the must is carried out before the cooling step, preferably with a filter press. Preferably, at least 95% of the must is separated and in an even more preferred manner all of the must is separated from the liquid. By "all" is understood here to relate to the separation method used.

Preferably, said enzymatic cocktail originating from the cooling step is mixed with the enzymes originating from the enzyme production step, Said cocktail is mixed in whole or in part.

Said cocktail, mixed or not, is used in enzymatic hydrolysis.

The residual must can be subjected to a new cooling step optionally, but preferably, followed by a separation of a new enzymatic cocktail.

The conditions of these steps are those described previously.

One additional cooling step is indicated here, but the number thereof is not limited. Thus, the invention also relates to a process implementing the preceding steps in which said residual must is subjected to a cooling step and an enzymatic cocktail, separated or not separated from the residual must, is obtained at the end of the cooling step. Preferably, said cocktail is separated from the residual must obtained at the end of said cooling step.

Preferably, the enzymatic cocktails originating from the cooling steps are mixed. Preferably, they are mixed with the enzymes originating from the enzyme production step.

Generally, it is possible to mix each of the cocktails with each other and/or with the enzymes originating from the enzyme production step. The proportion of each of the components of the mixture is determined according to the use of said mixture. Preferably, the cocktails and enzymes are mixed in their entirety.

At least one cocktail, mixed or not, is used in enzymatic hydrolysis.

BRIEF DESCRIPTION OF DRAWINGS

The invention will be better understood from FIGS. 1 to 6.

FIG. 7 is a photo of the *Trichoderma reesei* CL847 must after separation and before the cooling step.

FIG. 8 shows the change in the concentration of proteins in the culture supernatant.

FIG. 9 shows the β-glucosidase activity measured at the end of the production step and after cooling the fungus at 4° C. for 72 hours.

FIG. 10 shows the β-glucosidase activity measured at the end of the culture and after autolysis of the fungus at 4° and 20° C. for 72 hours.

FIG. 11 shows the specific β-glucosidase activity (IU/mg) obtained after the two separation series.

FIG. 12 shows the specific FPase activity (IU/mg) obtained after the two separation series.

FIG. 13 corresponds to the identification of the enzymes in the separation step.

Figure 1:
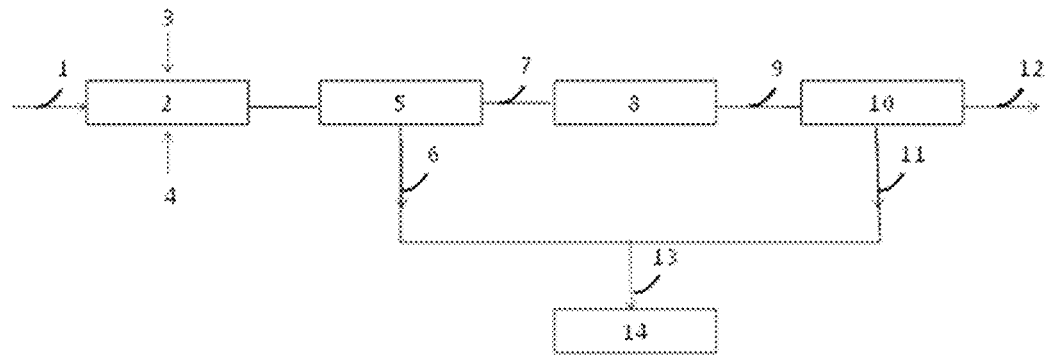
FIG. 1 describes the preferred embodiment with a separation step between the enzyme production step and the cooling step.

According to FIG. 1, a carbon source and an inductive source are introduced (pipe 1) into an enzyme production step (enzyme production zone 2), as well as a cellulolytic microorganism producing cellulases and/or hemi-cellulases (pipe 3) and the required nutrients (pipe 4).

The product obtained is separated (separation zone 5) into a liquid containing the enzymes (pipe 6) and a must is recovered (pipe 7) containing the fungus and enzymes held within.

The must is subjected to the cooling step (cooling zone 8).

In an embodiment, the liquid is drawn off from the enzyme production zone (reactor) and the must remains in said zone where it is cooled down.

In another preferred embodiment, the culture medium is drawn off from the enzyme production zone and separated in a separation means (filtration/pressing, centrifugation etc.), preferably after settling and drawing-off of the liquid, in order to obtain the must. This must is introduced into the cooling zone which can be the reactor of the enzyme production zone (in the case of a discontinuous process) or another reactor (in the case of a continuous process).

The cooled must (pipe 9) is separated (zone 10) into a liquid containing the enzymatic cocktail (pipe 11) and a solid which is the residual must (pipe 12).

The enzymes in the flows of pipes 6 and 11 are mixed and are sent (pipe 13) into the enzymatic hydrolysis zone (14).

Figure 3:
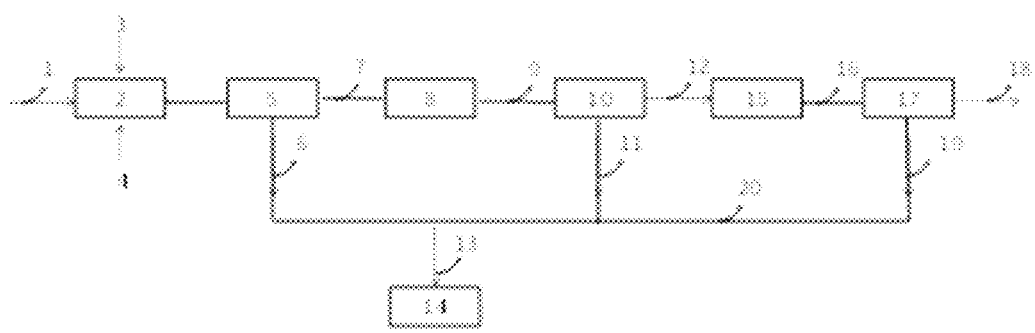
In FIGS. 3 and 4, an additional cooling step is added to FIGS. 1 and 2 respectively.

FIG. 3 repeats this diagram, adding a cooling step.

The residual must (must 12) is subjected to the additional cooling step (cooling zone 15).

In the same way as previously, the must sent into the additional cooling step (zone 15) may not have been separated in the zone 10 after the first cooling step (zone 8). The cooled must (pipe 16) is separated (zone 17) into a liquid containing the enzymatic cocktail (pipe 19) and a solid which is the residual must (pipe 18).

The enzymes in the flow of the pipe 19 are mixed with those of the flows originating from the enzyme production step (pipe 6), from the first cooling step (pipe 11) and are sent (pipe 20) into the enzymatic hydrolysis zone (14).

Figure 2:
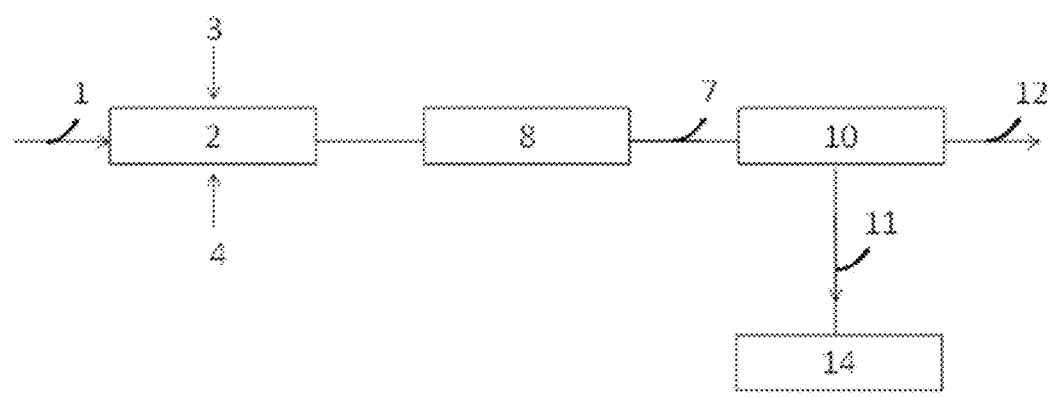
FIG. 2 is a representation without separation of the must.

The reference numbers of FIG. 1 will be recognized in FIG. 2. The separation step (zone 5) after the enzyme production step is omitted.

Figure 4:
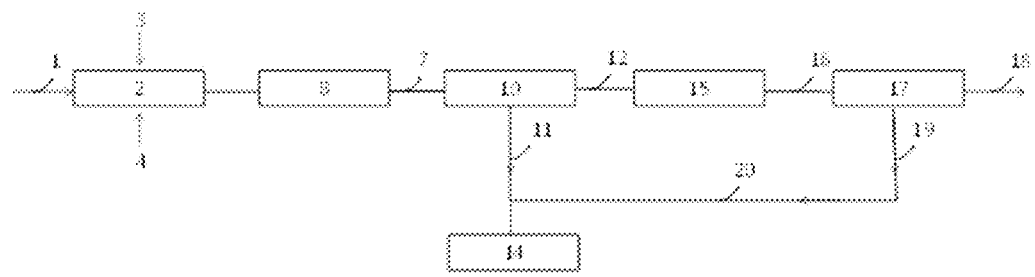

The same applies to FIG. 4 which is based on FIG. 2 and which includes the additional cooling step, the reference numbers relating to this addition are taken from FIG. 3.

Figure 5:
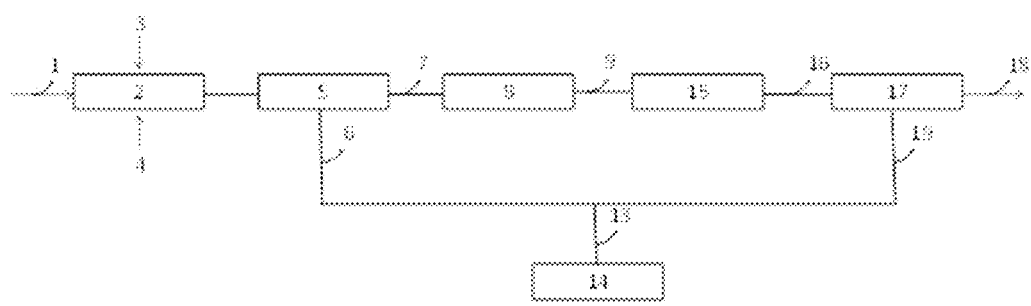
FIG. 5 shows an embodiment combining the presence or absence of separation.

It is also possible to combine in one diagram the presence of one separation and the absence of the other separation. This is for example illustrated in FIG. 5. This shows the presence of the separation at the end of the enzyme production step (zone 5), the absence of separation at the end of the first cooling step (zone 8) and before the additional cooling step, and the presence of separation after the additional cooling step (zone 17).

Figure 6:
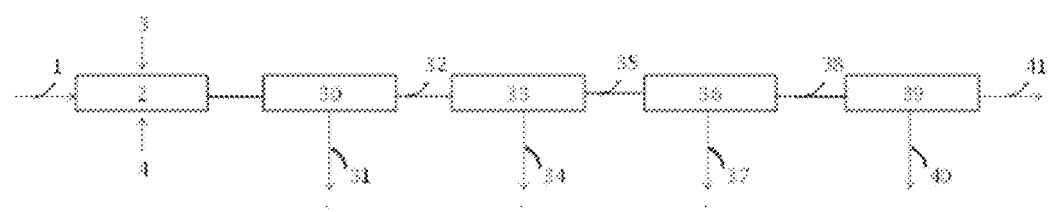
FIG. 6 shows a preferred embodiment of the must separation step before and/or after the cooling step.

FIG. 6 shows a preferred embodiment of the must separation step before and/or after the cooling step.

With reference to FIG. 1, this is an embodiment of zone 5 and/or of zone 10.

At the end of the enzyme production zone 2, the culture medium is separated in a settling step (zone 30), the fungus is located in the settled sludge (pipe 31) and the cloudy liquor obtained (pipe 32) passes into a centrifugation step (centrifugation zone 33). This results in a cream (pipe 34) containing the fungus and a clear liquor (pipe 35). In order to achieve the separation, the clear liquor passes into a microfiltration step (zone 36), the retentate (pipe 37) contains the fungus, and the permeate (pipe 38) contains the enzymes.

The different flows containing the fungus (sludge, cream, retentate) can be mixed and constitute the must which will be sent to the cooling step or constitute the residual must which will be subjected, or not subjected, to a new cooling step.

In order to concentrate the enzymes, the permeate is passed into an ultrafiltration step. A concentrated retentate of enzymes (pipe 40) is then obtained, as well as a permeate (pipe 41) which can be reused in the process.

It will be noted that all of the settling and centrifugation steps can be replaced by one filtration/pressing (filter/press).

EXAMPLES

Example 1: With FIGS. 7 to 9

Figure 7:
FIGS. 7 to 13 relate to the examples.

FIG. 7 is a photo of the *Trichoderma reesei* CL847 must after separation and before the cooling step.

Figure 8:
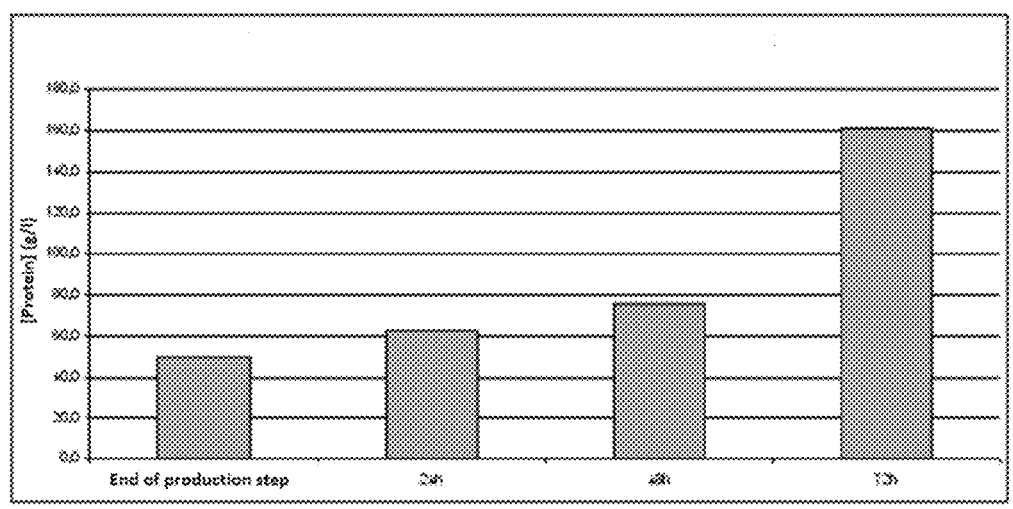

FIG. 8 shows the change in the concentration of proteins in the culture supernatant.

Figure 9:
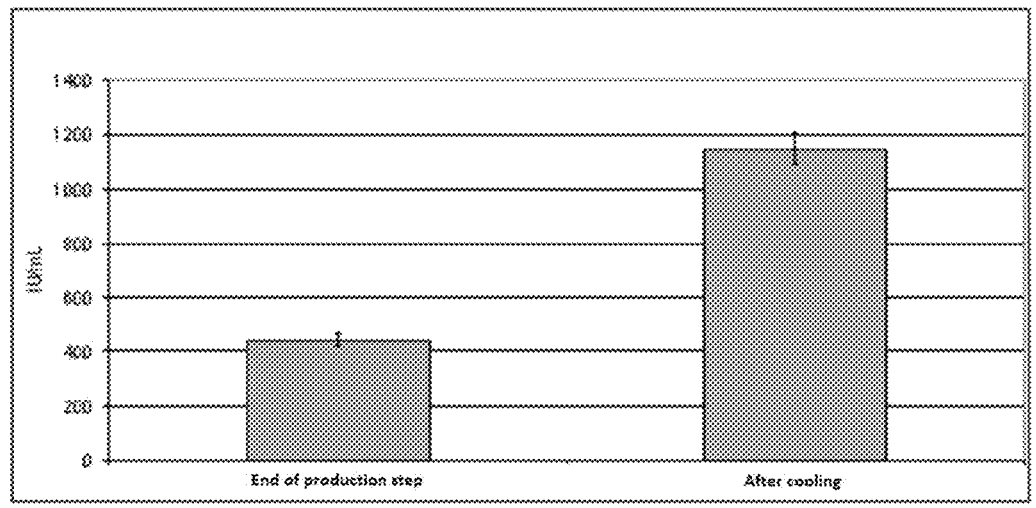

FIG. 9 shows the β-glucosidase activity measured at the end of the production step and after cooling the fungus at 4° C. for 72 hours.

The production of cellulases is carried out in a 20 L bioreactor (of which 12 L are useful) stirred mechanically. The mineral medium has the following composition: KOH 1.66 g/L, H3PO4 85% 2 mL/L, (NH4)2SO4 2.8 g/L, MgSO4.7 H2O 0.6 g/L, CaCL2 0.6 g/L, MnSO4 3.2 mg/L, ZnSO4.7 H2O 2.8 mg/L, CoCl2 10 4.0 mg/L, FeSO4.7 H2O 10 mg/L, Corn Steep 1.2 g/L, antifoaming agent 0.5 mL/L.

The bioreactor containing the mineral medium is sterilized at 120° C. for 20 minutes, the glucose carbon-containing source is sterilized separately at 120° C. for 20 minutes then added sterilely into the bioreactor so as to have a final concentration of 30 g/L. The bioreactor is seeded at 10%

(v/v) with a liquid pre-culture of the strain of *Trichoderma reesei* CL847. The mineral medium of the pre-culture is identical to that of the bioreactor apart from the addition of potassium phthalate at 5 g/L in order to buffer the pH. The growth of the fungus in the preculture is carried out using glucose as carbon-containing substrate, at a concentration of 30 g/L. The growth of the inoculum lasts from 2 to 3 days and is carried out at 28° C. in a stirred incubator. The transfer to the bioreactor is carried out if the residual glucose concentration is less than 15 g/L.

The production experiment carried out in the bioreactor comprises two phases:
  a growth phase on a glucose carbon-containing substrate (initial concentration=30 g/L) at a temperature of 27° C. and a pH of 4.8 (regulated with 5.5 M ammonia). Aeration is at 0.5 vvm and stirring is increased between 200 and 800 rpm depending on the pO2 (dissolved oxygen pressure), which is maintained higher than 30%.
  an enzyme production phase. When the original substrate of the fermenter is exhausted, a solution of lactose at 250 g/L is continuously injected at a flow rate of 35 to 45 mg per g of cells and per hour up to 164 hours. The temperature is reduced to 25° C. and the pH to 4 until the end of the culture. The pH is adjusted by the addition a 5.5 N solution of ammonia which supplies the nitrogen required for the synthesis of the excreted proteins. The dissolved oxygen content is maintained above 15 to 20% by the aeration and stirring action.

The production of enzymes is followed by assay of the extracellular proteins by the Lowry method and BSA standard, after separation of the mycelium by filtration or of cells formed). The final concentration of proteins obtained is equal to 45 g/L.

This production step was followed by separation of the fungal must from the culture supernatant. The must was pressed so as to extract a maximum amount of supernatant (FIG. 7) and weighed. The latter was placed in a closed container at 4° C. for 72 hours.

Samples of the supernatant released following the autolysis of the fungus were taken every 24 hours up to 72 hours The weight of the liquid was determined after 72 hours. It is equivalent to 30% of the weight of the must. Assays of the protein concentrations are shown in FIG. 8. It can be seen that the concentration is multiplied by 3 relative to the end of the enzyme production as well as the β-glucosidase activity (FIG. 9)

Example 2: With FIGS. 10 to 13

Figure 10:
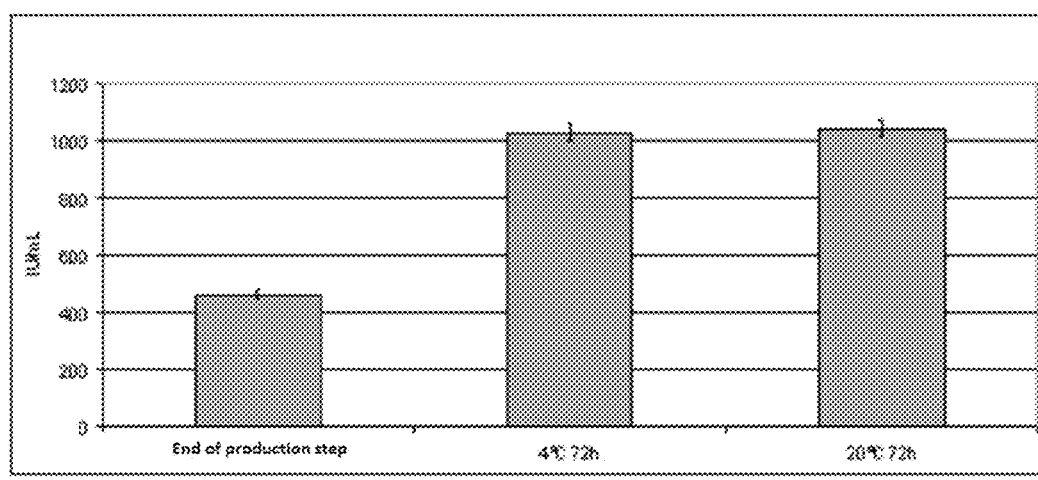

FIG. 10 shows the β-glucosidase activity measured at the end of the culture and after autolysis of the fungus at 4° and 20° C. for 72 hours.

Figure 11:
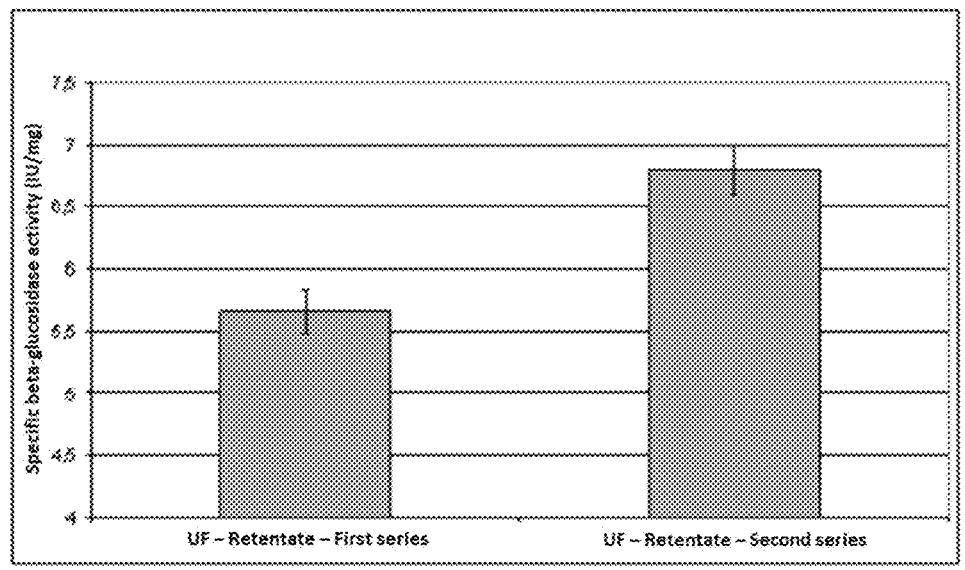

FIG. 11 shows the specific β-glucosidase activity (IU/mg) obtained after the two separation series.

Figure 12:
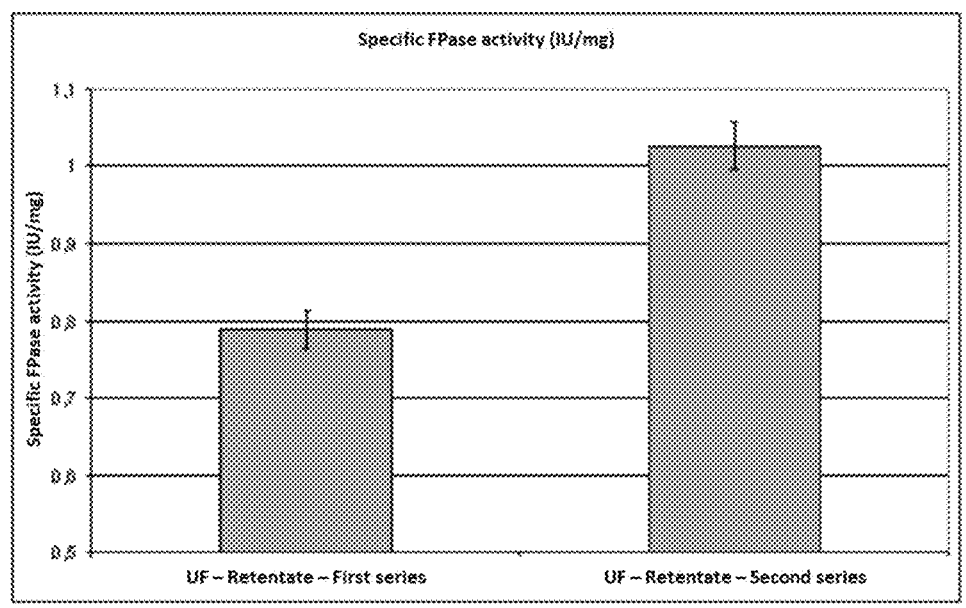

FIG. 12 shows the specific FPase activity (IU/mg) obtained after the two separation series.

Figure 13:
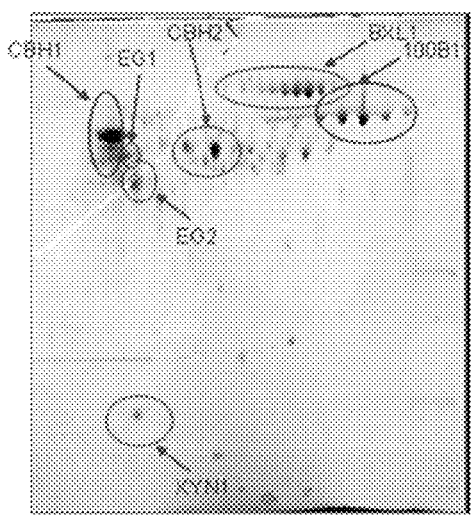
Figure 13:
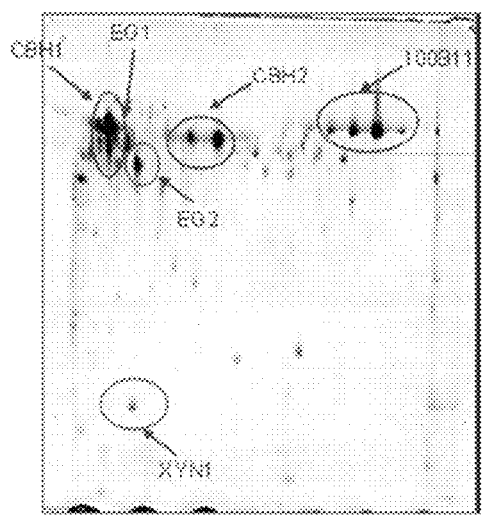

FIG. 13 corresponds to the identification of the enzymes in the separation step.

The process is implemented in a 6 m³ pilot unit. The fungus *Trichoderma reesei* CL847 is cultured under the same conditions described in Example 1. At the end of the production phase the enzymes are separated in 4 steps: a settling step, a centrifugation step, a microfiltration step and an ultrafiltration step.

These four steps are shown diagrammatically in FIG. 6. The first three steps serve to eliminate the fungus and the last step (ultrafiltration) serves to concentrate the enzymes produced.

All the fungal fractions recovered (settler sludge, centrifuge cream and microfiltration retentate), are placed in the bioreactor, cooled at 8° C. for 72 hours and diluted with water to a final volume equal to 4 m³. The must undergoes a second separation series: centrifuge, microfiltration and ultrafiltration.

The quantity of enzymes recovered at the end of the second separation series is similar to that obtained at the end of the first, i.e. approximately 70 kg of proteins after the first separation series and 64 kg after the second separation series.

By contrast, it is interesting to note that the β-glucosidase activity (FIG. 11) and the FPase activity (FIG. 12) specific to the enzymatic cocktail obtained are 20% greater after the cooling step (autolysis of the fungus). The enzymatic cocktail recovered is consequently much more effective.

Two-dimensional electrophoreses were carried out in order to see if there was a significant modification of the composition of the enzymatic cocktail during the separation steps. Starting from samples desalinated beforehand using FPLC [fast protein liquid chromatography], with 200 μg deposits on the 2D gel, and Coomassie blue staining, the proteins are separated according to their molecular mass and their isoelectric point.

The scanned gels are shown in FIG. 13; FIG. 13*a* corresponds to the cream and FIG. 13*b* to the clear liquor.

The main enzymes were identified in the centrifugation step in the clear liquor and the cream. A significant difference was noted in the profiles of the gels. The centrifugation creams show β-xylosidases. This activity was measured on pnp-xylose for confirmation and a specific activity was found which was approximately 3 times greater in the creams than in the enzymatic cocktail obtained at the end of production (1.2 IU/mg in the creams and 0.4 IU/mg in the final sample from the fermenter).

The invention claimed is:

1. A process for the production of an enzymatic cocktail from a cellulolytic microorganism producing cellulases and/or hemi-cellulases, where the microorganism is a filamentous fungus comprising:
  a—producing enzymes to obtain a medium containing enzymes and a microorganism must, and separating said must from the liquid containing said enzymes,
  b—cooling said must to a temperature between 4 and 20° C., which is a temperature below the temperature of the enzyme production step, for a time of 12 to 90 hours such that:
    the beta-glucosidase or β-xylosidase concentration of liquid originating from cooling is greater than that of the liquid originating from the enzyme production (a), and/or
    the solid volume/total volume ratio is less than said ratio for the enzyme production and
  c—obtaining an enzymatic cocktail at the end of cooling (b).

2. The process according to claim 1 in which said separated must is diluted with water.

3. The process according to claim 1 in which, after cooling (b), the enzymatic cocktail originating from the must is separated and a residual must is obtained.

4. The process according to claim 1 in which the separation takes place by at least one centrifugation or filtration/pressing or microfiltration, optionally preceded by settling.

5. The process according to claim 3 in which the enzymes of the separated liquid are concentrated.

6. The process according to claim 1 in which cooling (b) is carried out at a pH between 3.5 and 5.5.

7. A process for the production of an enzymatic cocktail from a cellulolytic microorganism producing cellulases and/or hemi-cellulases, where the microorganism is a filamentous fungus comprising:
   a—producing enzymes to obtain a medium containing enzymes and a microorganism must, optionally separating said must from the liquid containing said enzymes,
   b—cooling said must to a temperature between 4 and 20° C., which is a temperature below the temperature of the enzyme production step, for a time such that:
      the beta-glucosidase or β-xylosidase concentration of the liquid originating from cooling is greater than that of the liquid originating from the enzyme production (a), and/or
      the solid volume/total volume ratio is less than said ratio for the enzyme production, and
   c—obtaining an enzymatic cocktail is obtained at the end of cooling (b), in which cooling (b) is carried out in an atmosphere depleted of oxygen.

8. A process for the production of an enzymatic cocktail from a cellulolytic microorganism producing cellulases and/or hemi-cellulases, where the microorganism is a filamentous fungus comprising:
   a—producing enzymes to obtain a medium containing enzymes and a microorganism must, optionally separating said must from the liquid containing said enzymes,
   b—cooling said must to a temperature between 4 and 20° C., which is a temperature below the temperature of the enzyme production step, for a time such that:
      the beta-glucosidase or β-xylosidase concentration of the liquid originating from cooling is greater than that of the liquid originating from the enzyme production (a), and/or
      the solid volume/total volume ratio is less than said ratio for the enzyme production, and
   c—obtaining an enzymatic cocktail is obtained at the end of cooling (b), in which in cooling (b), a neutral gas is injected.

9. The process according to claim 1 in which the microorganism belongs to the genus *Trichoderma*.

10. The process according to claim 3 in which said residual must is subjected to cooling and an enzymatic cocktail, optionally separated from the residual must, is obtained at the end of the cooling.

11. The process according to claim 10 in which enzymatic cocktails originating from production of separate must are mixed.

12. The process according to claim 1 in which at least one enzymatic cocktail is mixed with separated liquid containing enzymes and originating from the enzyme production (a).

13. A process for enzymatic hydrolysis of a feed, comprising subjecting said feed to at least one enzymatic cocktail obtained according to claim 1.

14. The process according to claim 9, wherein the microorganism belongs to *Trichoderma reesei*.

15. The process according to claim 14, wherein the microorganism belongs to the strain CL 847.

16. The process according to claim 7, wherein cooling is carried out in an anaerobic atmosphere.

17. The process according to claim 8, wherein the cooling gas is carbon dioxide or nitrogen.

18. A process for the production of an enzymatic cocktail from a cellulolytic microorganism producing cellulases and/or hemi-cellulases, where the microorganism is a filamentous fungus comprising:
   a—producing enzymes to obtain a medium containing enzymes and a microorganism must, and separating said must from the liquid containing said enzymes,
   b—cooling said must to a temperature between 4 and 20° C., which is a temperature below the temperature of the enzyme production step, for a time of 12 to 90 hours such that:
      the beta-glucosidase or β-xylosidase concentration of liquid originating from cooling is greater than that of the liquid originating from the enzyme production (a), and/or
      the solid volume/total volume ratio is less than said ratio for the enzyme production and
   c—obtaining an enzymatic cocktail at the end of cooling (b),
   by mixing the liquid containing said enzymes from (a) and the liquid originating from cooling in (b).

* * * * *